US009783429B2

(12) United States Patent
Nakagawa et al.

(10) Patent No.: US 9,783,429 B2
(45) Date of Patent: Oct. 10, 2017

(54) METHOD FOR PURIFYING DODECACARBONYL TRIRUTHENIUM

(71) Applicant: TANAKA KIKINZOKU KOGYO K.K., Chiyoda-ku, Tokyo (JP)

(72) Inventors: Hirofumi Nakagawa, Tsukuba (JP); Tasuku Ishizaka, Tsukuba (JP); Hirofumi Ishida, Tsukuba (JP); Akiko Kumakura, Tsukuba (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 0 days.

(21) Appl. No.: 15/312,355

(22) PCT Filed: Jun. 2, 2015

(86) PCT No.: PCT/JP2015/065832
§ 371 (c)(1),
(2) Date: Nov. 18, 2016

(87) PCT Pub. No.: WO2015/186679
PCT Pub. Date: Dec. 10, 2015

(65) Prior Publication Data
US 2017/0107118 A1    Apr. 20, 2017

(30) Foreign Application Priority Data
Jun. 4, 2014  (JP) .................................. 2014-115440

(51) Int. Cl.
*C01G 55/00* (2006.01)
(52) U.S. Cl.
CPC .................. *C01G 55/008* (2013.01)
(58) Field of Classification Search
CPC .............................. C01G 55/00; C01G 55/008
See application file for complete search history.

(56) References Cited

U.S. PATENT DOCUMENTS

2014/0057050 A1*  2/2014  Saito .................... C23C 16/30
427/252

FOREIGN PATENT DOCUMENTS

| JP | 2008-244298 A | 10/2008 |
| JP | 2013-36054 A | 2/2013 |
| WO | WO 2013/018577 A1 | 2/2013 |

OTHER PUBLICATIONS

PCT, International Search Report of PCT/JP2015/065832, dated Aug. 18, 2015.

(Continued)

*Primary Examiner* — Daniel C McCracken
(74) *Attorney, Agent, or Firm* — Orrick, Herrington & Sutcliffe, LLP; Joseph Calvaruso

(57) ABSTRACT

An object of the present invention is to provide a purification method to give dodecacarbonyl triruthenium (DCR) which serves as a raw material for chemical vapor deposition and does not cause the contamination of a thin film with impurities even when used to form a ruthenium thin film. The present invention relates to a method in which the dissolved oxygen concentration in the solvent is made 0.2 mg/L or less in at least a dissolution stage, and an organic ruthenium compound including DCR as a raw material for chemical vapor deposition is purified by a recrystallization method. The present invention allows a trace amount of impurities to be separated from DCR. When a ruthenium thin film is formed by use of DCR thus obtained, the formed film is hardly contaminated with impurities. Additionally, the purification method of the present invention is also applicable for recovering/purifying DCR after being used for the formation of a ruthenium thin film.

20 Claims, 5 Drawing Sheets

(56) References Cited

OTHER PUBLICATIONS

Green, Chemical Vapor Deposition of Ruthenium and Ruthenium Dioxide Films, J. Electrochem. Soc., 1985, vol. 132, issue 11, pp. 2677-2685.

* cited by examiner

NITROGEN GAS

1% OXYGEN-CONTAINING GAS

METHOD FOR PURIFYING DODECACARBONYL TRIRUTHENIUM

TECHNICAL FIELD

The present invention relates to a method for purifying dodecacarbonyl triruthenium, which is useful as a raw material for forming a ruthenium thin film or a ruthenium compound thin film by a chemical vapor deposition method.

BACKGROUND ART

In the formation of a ruthenium thin film or a ruthenium compound thin film by a chemical vapor deposition method such as chemical vapor deposition (CVD) or atomic layer vapor deposition (ALD), as raw material compounds therefor, a large number of organic ruthenium compounds is known. Among such organic ruthenium compounds, in recent years, dodecacarbonyl triruthenium represented by following formula (hereinafter referred to as DCR) is hoped to be put to practical use.

[Chemical Formula 1]

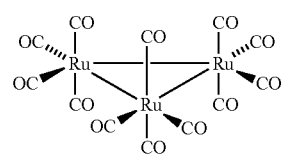

DCR is a substance having a melting point of 154 to 155° C., which is solid (orange crystalline) at normal temperature. DCR has a simple molecular structure composed only of Ru and CO, and film can be formed only by thermal decomposition, without use of a reactant gas. Further, in the formed thin film, impurities, such as hydrocarbon, are less likely to remain. Additionally, even though DCR is a solid material, the thin film production efficiency is not adversely affected when the material container is regulated, or the process is suitably controlled. Therefore, its utilization is expected.

Examples of a known production method for such DCR include a method in which a ruthenium compound is carbonylated to synthesize DCR, and then the synthesized DCR is purified (Patent Document 1). When such DCR after synthesis is used for the formation of a ruthenium thin film in an unpurified state, ignition may occur upon the opening of the material container for thin film formation. As a cause of such ignition, the presence of impurity elements such as Fe, Al, and Cr in DCR after synthesis, which are derived from and incorporated from the raw material or the constituent materials of the equipment, can be mentioned. Therefore, DCR after synthesis is preferably subjected to a purification step, such as a sublimation method.

DCR has the property of easily sublimating at a reduced pressure, and thus is suitable for purification by a sublimation method. Specifically, when DCR having a high sublimation pressure is preferentially sublimated and recovered, impurity elements having a low sublimation pressure, such as Fe, can be separated from DCR. The operation process of a sublimation method is relatively simple. Therefore, the loss of the desired material is low, and the purity of DCR can be efficiently improved.

RELATED ART DOCUMENT

Patent Documents

Patent Document 1: JP 2013-036054 A

SUMMARY OF THE INVENTION

Problems to be Solved by the Invention

However, when a ruthenium thin film is formed by a chemical vapor deposition method using DCR purified by the sublimation method, the formed ruthenium film is sometimes contaminated with a small amount of impurities. To specify the cause of such contamination with impurities, the raw material DCR was observed, but no specific problems was found.

Thus, an object of the present invention is to provide a purification method to give DCR, which is DCR to serve as a raw material for chemical vapor deposition, and does not cause the contamination of a thin film with impurities even when used to form a ruthenium thin film.

Means for Solving the Problems

To solve the above problems, the present inventors examined the optimization of a purification method by a recrystallization method. Although a sublimation method is useful in that low-sublimability elements such as Fe can be separated, separation is impossible when the contained impurities have sublimability like DCR. Additionally, although a sublimation method can efficiently reduce impurities in a relatively simple process, separation is difficult when the amount of impurities is extremely small. In contrast, in a recrystallization method, use of the difference in solubility in a predetermined solvent between DCR and impurities, even a trace amount of impurities can be removed. In particular, DCR after synthesis or DCR purified by a sublimation method may contain organic components derived from unreacted raw materials, various kinds of dust, and the like. When such organic components are contained, DCR and the organic components can be separated by selecting a suitable solvent.

Thus, the present inventors conducted research about methods for purifying DCR applying a recrystallization method. However, when conventionally known recrystallization methods are simply applied, gray impurities (hereinafter referred to as "gray substance") are sometimes contained in DCR after recrystallization. Since this gray substance is not seen before recrystallization, it is considered to have been formed by any cause during the recrystallization step. Thus, the present inventors conducted extensive research about conditions under which, while applying a recrystallization method, the above gray substance is not formed after recrystallization, and thus accomplished the present invention as follows.

The present invention relates to a method for purifying dodecacarbonyl triruthenium (DCR), for purifying, by a recrystallization method, an organic ruthenium compound including DCR represented by the following formula as a raw material for chemical vapor deposition:

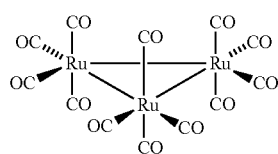

[Chemical Formula 1]

the method including a recrystallization step of purifying DCR by a recrystallization method, the recrystallization step including a dissolution stage of dissolving DCR in a solvent, a precipitation stage of precipitating DCR from the solvent, and a recovery stage of recovering the precipitated DCR, wherein at least the dissolution stage is performed with a dissolved oxygen concentration in the solvent being 0.2 mg/L or less.

In the purification method of the present invention, during the recrystallization step, the dissolved oxygen concentration in a solvent is maintained at 0.2 mg/L or less at least at a dissolution stage. According to this method, impurities contained in DCR can be separated even when the amount thereof is only trace, and, at the same time, a gray substance is not formed after recrystallization. Then, when a ruthenium thin film is formed by use of DCR purified by the present invention, the formed film is hardly contaminated with impurities.

Here, in the present invention, the limitation of the dissolved oxygen concentration in the solvent as above is based on the detailed study of the characteristics of the gray substance and its formation factors as follows. First, with respect to the gray substance, as a result of elemental analysis, infrared spectroscopic (IR) analysis, and thermal decomposition (TG) analysis, the composition and characteristics thereof were obviously different from those of pure DCR. Meanwhile, the gray substances was sometimes formed even when DCR after synthesis was purified by a sublimation method and then purified by a general recrystallization method. From this fact, it is considered that the gray substance has sublimability, that is, it is sublimated together with DCR in the sublimation step, and also has solubility, that is, it is dissolved/precipitated together with DCR in the recrystallization step. From above, although the gray substance is obviously different from DCR in constituent elements and characteristics, such as heat decomposability, its characteristics are close to DCR in sublimability and solubility. From the above examination results, the present inventors conceived that the gray substance is a by-product resulting from the decomposition of DCR. They also conceived that the formation of such a by-product is caused by the reaction between DCR and oxygen during the recrystallization step, and thus accomplished the present invention.

Hereinafter, each stage of the method for purifying DCR will be described in detail in order from the acquisition of DCR to be purified to the recrystallization step.

DCR to be purified in the present invention can be obtained by a generally known synthesis method. To obtain DCR by a synthesis method, a method in which a ruthenium salt as a raw material is carbonylated can be utilized. Specifically, a method in which a ruthenium salt is directly carbonylated with carbon monoxide (hereinafter referred to as "direct method") is preferable. Aside from the direct method, for example, a synthesis method in which, using a ruthenium salt as a raw material, acetylacetonato ruthenium is obtained as an intermediate, and the intermediate is carbonylated, is also known. However, a method via an intermediate has an increased number of steps, increasing the chance of contamination with impurities. When DCR is synthesized by a direct method, the reaction conditions are preferably as follows: reaction pressure: 0.2 to 0.9 MPa, reaction temperature: 50 to 100° C., reaction time: 10 to 30 hours.

As a ruthenium salt to serve as a raw material in the direct method, ruthenium chloride, ruthenium oxide, ruthenium nitrate, hexamine ruthenium chloride, and ruthenium acetate are preferable, and ruthenium chloride is particularly preferable. This is because these raw materials are commercially available substances and easy to obtain. Additionally, as a raw material, high-purity substances are preferable. Incidentally, in the synthesis of an organometallic compound such as DCR, auxiliary metals having catalytic activity are often used. However, in the present invention, the addition of auxiliary metals is not necessary. This is because the application of an auxiliary metal may be a cause of contamination with impurities.

Although DCR to be purified in the present invention may be obtained by the synthesis methods described above, besides them, commercially available DCR may also be used. Additionally, after DCR is used for thin film formation, the used DCR can be recovered and subjected to purification. Reuse of used ruthenium, which is an effective resource, makes it possible to achieve stable supply of ruthenium.

DCR described above is subjected to a purification step. In the purification step, only a recrystallization step may be performed, but preferably, a sublimation step is also performed additionally to the recrystallization step, and particularly preferably, the recrystallization step is performed after the sublimation step. A sublimation method is suitable when elements such as Fe are contained in DCR, and is also effective in that when the impurity content is high, the impurities can be efficiently separated. Thus, when DCR having the impurity content previously reduced to some extent in the sublimation step is subjected to purification, a trace amount of impurities contained in DCR after sublimation can be efficiently removed by a recrystallization method.

To a sublimation step, a known sublimation method can be applied. Preferred conditions are as follows, for example: sublimation temperature: 80 to 120° C., sublimation pressure: 80 Pa or less.

In the recrystallization step, the subject is preferably DCR from which elements such as Fe have been previously separated in the above sublimation step. However, DCR synthesized by a direct method may also be directly used. As the specific procedure of the recrystallization step, the stages (1) to (5) are performed in order. Among them, the filtration stage (2) and the drying stage (5) can be omitted.

(1) Stage in which DCR is dissolved in a solvent (dissolution stage)
(2) Stage in which the solvent with dissolved DCR is filtered (filtration stage)
(3) Stage in which DCR is precipitated from the solvent (precipitation stage)
(4) Stage in which precipitated DCR is recovered (recovery stage)
(5) Stage in which recovered DCR is dried (drying stage)

Hereinafter, purification conditions in each of the above stages will be described in detail. In the dissolution stage where solid-state DCR is dissolved in a solvent, the dissolved oxygen concentration of the solvent is to be 0.2 mg/L or less. To maintain the dissolved oxygen concentration in the solvent at 0.2 mg/L or less, the oxygen concentration in the atmosphere gas inside the reaction vessel containing the solvent is preferably also reduced. Therefore, the oxygen concentration in the atmosphere inside the reaction vessel is preferably 0.07 vol % or less, and particularly preferably 0.1 vol % or less. The lower limit is not particularly set. However, considering that the range of oxygen concentrations to which the oxygen concentration inside the vessel can be reduced by a general method is limited, the lower limit will be about 0.04 vol %.

As a method for reducing the dissolved oxygen concentration in the solvent or the oxygen concentration in the atmosphere inside the reaction vessel as described above, an optional technique may be employed, such as a method in which an inert gas is fed into the solvent to cause bubbling, thereby reducing the dissolved oxygen concentration, or a method in which the gas in the atmosphere is replaced with an inert gas. To achieve the oxygen concentration specified in the present invention (a dissolved oxygen concentration in the solvent of 0.2 mg/L or less, or an atmosphere having an oxygen concentration of 0.1 vol % or less) by such a technique, although this depends on the size of the reaction vessel or the amount of solvent, it is required to perform the bubbling for a relatively long period of time, or the inert gas replacement several times. Thus, the present invention sets the upper limit of the oxygen concentration with a relatively precise value to reliably suppress the formation of a gray substance. Incidentally, as an inert gas to bubble the solvent or to replace the gas in the atmosphere, a known inert gas such as nitrogen gas or argon gas is applicable.

As the solvent applied in the dissolution stage, those having high solubility for DCR during heating and low solubility during cooling, and also having significantly lower solubility for impurities as compared with DCR or having significantly higher solubility, whereby precipitation does not occur even during cooling, are preferable. Examples of solvents that satisfy these requirements include acetone, dichloromethane, DMF, ethyl acetate, chloroform, toluene, acetonitrile, and THF. Such a solvent is preferably previously distilled, for example, to remove impurities in the solvent, and then used in the dissolution stage. Additionally, the solvent may optionally be heated to reliably dissolve DCR. In such a case, the solvent temperature is preferably within a range of 55 to 130° C.

In the following precipitation stage, DCR dissolved in the solvent is precipitated. Additionally to the dissolution stage, also in this precipitation stage, the dissolved oxygen concentration in the solvent (and the oxygen concentration in the atmosphere) is preferably maintained within the above range. In particular, when the solvent is heated in the dissolution stage, a gray substance tends to be formed by the reaction with oxygen. Therefore, the oxygen concentration is preferably maintained within the above range at least while the solvent temperature is high. When the solvent is heated in the dissolution stage, in this precipitation stage, the solvent is preferably cooled to 5 to 30° C. to precipitate DCR.

After the above precipitation stage, in the recovery stage, crystalline DCR precipitated using an arbitrary filtration method or the like is recovered. DCR after recovery contains a small amount of solvent, and thus the following drying stage is preferably performed.

The drying stage is preferably performed by vacuum drying. As described above, in the dissolution stage or the like, the oxygen concentration is reduced by bubbling with use of an inert gas, for example. However, in the drying stage, the oxygen concentration in the atmosphere is preferably reduced by reducing the pressure in the drying vessel, without use of an inert gas. This is because although the formation of a gray substance can be suppressed by reducing the oxygen concentration with use of an inert gas in the dissolution stage or the precipitation stage, in the case where an inert gas is used in the drying stage, even when the oxygen concentration is 0.1 vol % or less, a gray substance may be formed although any detailed reason therefor is unknown. Therefore, the drying stage is preferably performed at a reduced pressure of 500 Pa or less, and use of an inert gas should be avoided. Under the above reduced-pressure conditions, the oxygen concentration in the atmosphere in the drying vessel is likely to be 0.1 vol % or less. The above drying stage is preferably performed at 0 to 40° C.

Incidentally, after the dissolution stage and before the precipitation stage, an optional filtration stage may be performed. Through the filtration stage, impurities insoluble in the solvent can be removed from the solvent with dissolved DCR. When the filtration stage is omitted, a method in which the amount of solvent is reduced, and the solvent is removed by evaporation, may be applied.

Advantageous Effects of the Invention

As described above, in the purification method of the present invention, impurities can be separated from DCR even when the amount of contaminating impurities is trace. Additionally, when DCR obtained by the method of the present invention is used to form a ruthenium thin film, the contamination of the formed film with impurities can be avoided. Additionally, the purification method of the present invention is also applicable for recovering/purifying DCR from a used compound after the formation of a thin film.

DESCRIPTION OF EMBODIMENTS

Hereinafter, best modes for carrying out the present invention will be described.

Figure 1:
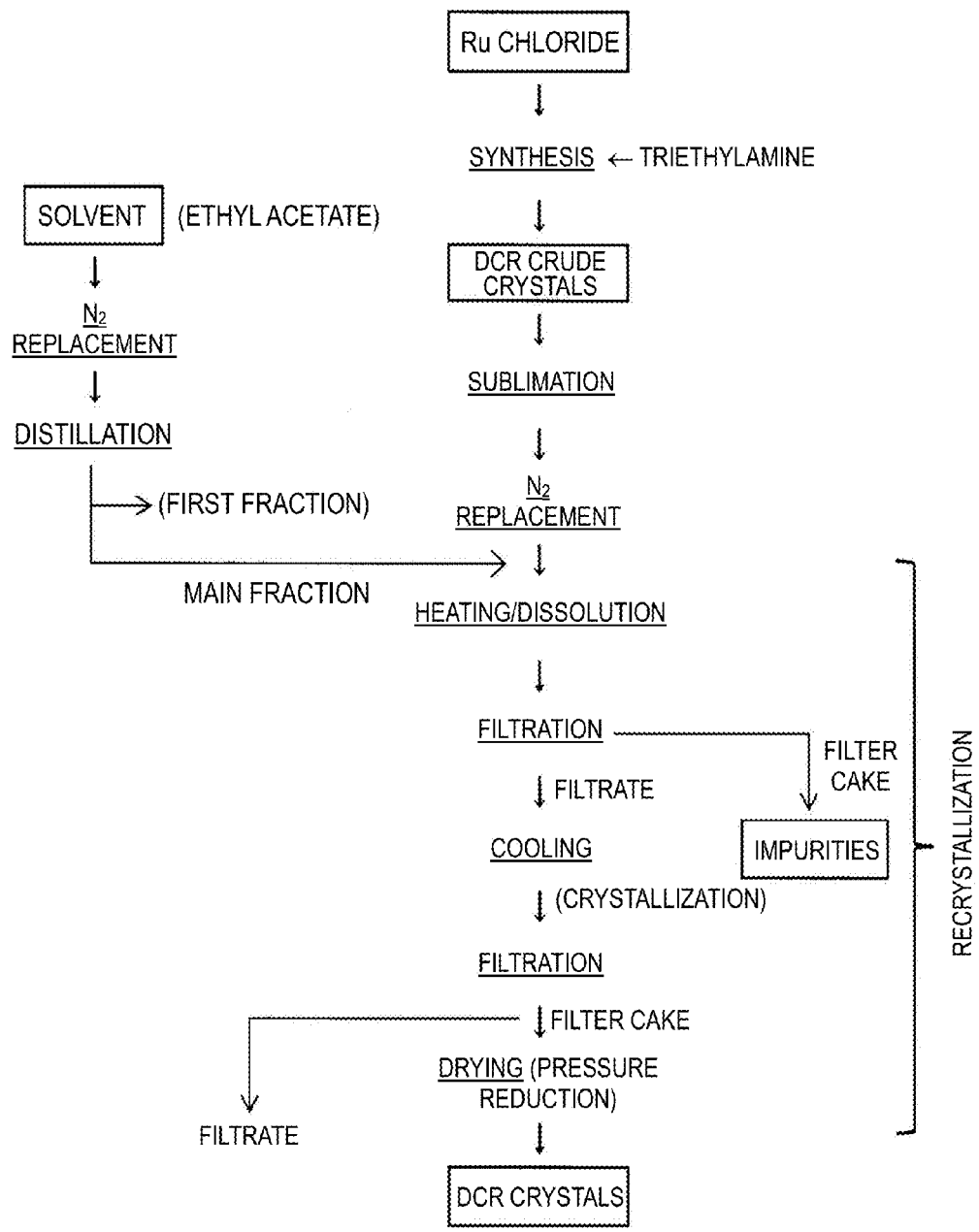
FIG. 1 is a flow diagram of the steps of the Example in the embodiment.

From ruthenium chloride as a raw material, DCR crude crystals were synthesized by a direct method, followed by purification by a sublimation method and a recrystallization method. During purification, nitrogen gas was supplied to reduce the oxygen concentration (Example), or nitrogen gas was not supplied (Comparative Example 1); DCR obtained by purification in each case was evaluated. FIG. 1 shows a process flow diagram about the Example.

Synthesis of DCR Crude Crystals 158 g of ruthenium chloride (manufactured by Tanaka Kikinzoku Kogyo K.K., ruthenium content: 38.67%, chlorine content: 47.4 wt %) and 6000 ml of 1-propanol were mixed and stirred, and the mixture was introduced into an autoclave having a volume of 10 L (made of steel) to serve as a reaction vessel. Then, 269 g of triethylamine was added to the reaction vessel, and further carbon monoxide gas was enclosed to 0.35 MPa. While supplying carbon monoxide to maintain the above reaction pressure, the reaction temperature was increased to 85° C. to allow the DCR synthesis reaction to proceed. The solution was allowed to react for 17 hours with stirring. After the synthesis reaction, the reaction mixture was cooled and filtered, and the filtrate was isolated to give 116 g of orange DCR crude crystals. The purity of the DCR crude crystals was 99%.

Sublimation Step

First, the DCR crude crystals obtained above were purified by a sublimation method. In the sublimation step, the DCR crude crystals were placed in a pear-shaped sublimator, and sublimation was performed under the following conditions.

Degree of vacuum: 1 Pa
Temperature: 95° C.
Sublimation time: 6 hours
Cooling water temperature: 8° C.

After the completion of the sublimation step, the DCR crude crystals collected in the cooling unit were subjected to ICP-MS to measure the contents of impurity elements. As a result, the contents of Fe, Li, Na, Mg, Al, Ca, K, Ti, V, Cr, Mn, Co, Ni, Cu, Zn, Sr, Y, Mo, Ir, Pt, Au, Pb, Th, and U were all 1 ppm or less.

Figure 2:
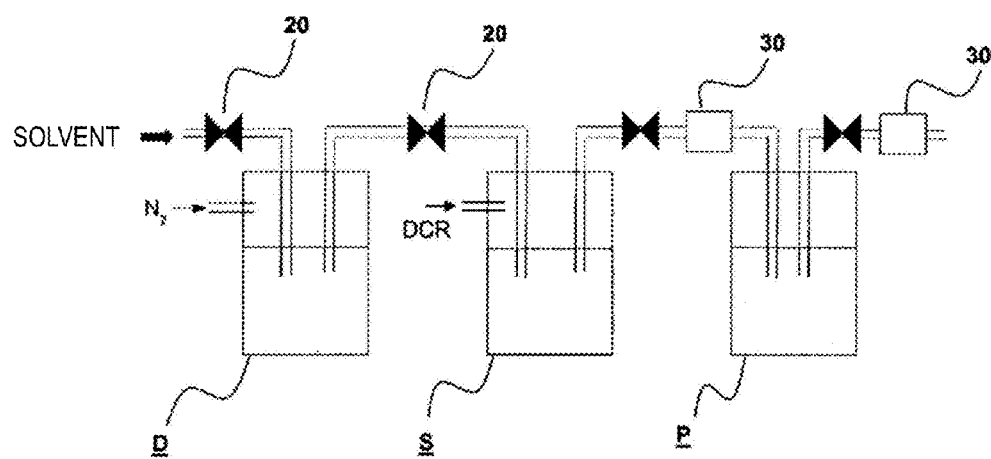
FIG. 2 is a schematic diagram of a recrystallization equipment in the embodiment.

Then, the DCR crude crystals after the sublimation step were purified by the following recrystallization method. In this embodiment, the recrystallization equipment shown in FIG. 2 was used. This recrystallization equipment includes a distillation tank (D) to previously distill the solvent in which DCR crude crystals are to be dissolved, a dissolution tank (S) to dissolve DCR crystals, and a crystallization tank (P) to precipitate DCR, and is configured such that a solvent and an inert gas can be supplied to the distillation tank D. Additionally, DCR crude crystals can be introduced into the dissolution tank S. The tanks are connected to one another through pipes capable of transporting the solutions in the tanks, and each pipe is provided with a valve 20. The pipes that transport solutions from the dissolution tank S and the crystallization tank P are each provided with a filtration means 30.

In purification with the above recrystallization equipment, the oxygen concentration in the atmosphere inside each tank can be reduced by the following procedure. Specifically, with the valves 20 of the distillation tank D, the dissolution tank S, and the crystallization tank P being all open, the pressure in each tank was reduced. Subsequently, an inert gas was supplied to the distillation tank D to replace the atmosphere gases in the dissolution tank S and the crystallization tank P and distillation tank D connected thereto with the inert gas. By repeating the inert gas replacement several times, the oxygen concentration in the atmosphere in each tank can be reduced to a predetermined amount or lower. Then, when a solvent is introduced into the recrystallization equipment in which the oxygen concentration in the atmosphere has been reduced as above, the dissolved oxygen concentration in the solvent also becomes a predetermined amount or lower, making it possible to achieve an oxygen concentration suitable for the following purification method.

Oxygen Concentration Check Test

Here, the value of the oxygen concentration in the atmosphere and that of the dissolved oxygen concentration in the solvent when the atmosphere gas in each tank is replaced with an inert gas by use of the above recrystallization equipment were checked. Specifically, the above recrystallization equipment was released to the air for 10 minutes, and then the pressure in the equipment was reduced to 0.09 MPa or less. Subsequently, the entire equipment was purged with nitrogen gas (99.99% nitrogen) from the distillation tank, and then the valve of each tank was closed. This nitrogen gas purge was repeated four times. Additionally, in the dissolution tank (S) and crystallization tank (P) purged with nitrogen gas, 5 L of ethyl acetate was placed. The oxygen concentration in the atmosphere in each tank was measured with an oximeter; the results are shown below. Incidentally, the following results are values after 3 minutes from when the gas in each tank is passed through the oximeter. Provided that the amount of dissolved oxygen in ethyl acetate in the air is 43.23 mg/L, the dissolved oxygen concentration in the solvent was calculated from the linear relationship with the oxygen concentration in the atmosphere. Additionally, when the nitrogen gas was replaced four times, the dissolved oxygen concentration in the solvent in each tank was actually measured; the results are shown below.

TABLE 1

Oxygen concentration in atmosphere in each tank (vol %)

| The number of replacements | Distillation tank | Dissolution tank | Crystallization tank |
|---|---|---|---|
| 0 | 21.9 | 19.6 | 22 |
| 2 | 0.005 | 0.242 | 0.136 |
| 3 | 0.004 | 0.064 | 0.05 |
| 4 | 0.004 | 0.044 | 0.044 |

TABLE 2

Dissolved oxygen concentration in solvent (mg/L)

| The number of replacements | Dissolution tank | Crystallization tank |
|---|---|---|
| 0 | 39.6 | 44.4 |
| 2 | 0.49 | 0.27 |
| 3 | 0.13 | 0.10 |
| 4 | 0.08 (0.05)* | 0.08 (0.05)* |

*In parentheses are actual measured values.

From above, when the atmosphere gas was replaced with nitrogen gas three times or more, the oxygen concentration in each tank of the recrystallization equipment was made 0.1 vol % or less. Additionally, when the nitrogen gas replacement was performed three times or more, the dissolved oxygen concentration in the solvent was 0.2 mg/L or less. Additionally, from the results of performing the replacement four times shown in Table 2, it was confirmed that the calculated value of the dissolved oxygen concentration in the solvent is almost equal to the actual measured value.

EXAMPLE

With the above recrystallization equipment, DCR crude crystals were purified by a recrystallization method. First, as a solvent, 5.3 L of ethyl acetate was placed in the distillation tank. The inside of the distillation tank with the valve closed was replaced with nitrogen gas four times, making the dissolved oxygen concentration in the solvent 0.2 mg/L or less and the oxygen concentration 0.1 vol % or less. Subsequently, ethyl acetate was distilled. 300 ml of the initial fraction was discarded, and 5 L of the main fraction was collected and used for the dissolution step.

Next, 100 g of DCR crude crystals were placed in the dissolution tank, the inside of the dissolution tank with the valve closed was replaced with nitrogen gas four times, and then 5 L of ethyl acetate distilled above (main fraction) was placed therein. At this time, the dissolved oxygen concentration in the solvent was 0.2 mg/L or less, and the oxygen concentration was 0.1 vol % or less. Then, ethyl acetate was heated to 75° C. to completely dissolve DCR. After the dissolution of DCR, the solution was filtered to remove impurities insoluble in ethyl acetate. The filtrate obtained after filtration was placed in the crystallization tank, which had been previously replaced with nitrogen gas four times to make the dissolved oxygen concentration in the solvent 0.2 mg/L or less and the oxygen concentration 0.1 vol % or less. The solution in the crystallization tank was cooled to 20° C. and then filtered, and the precipitated DCR crystals were collected. Subsequently, in a drying furnace having a reduced pressure of 500 Pa, DCR was dried at 23° C. for 48 hr. The obtained DCR was about 85 g.

Comparative Example 1

Figure 3:
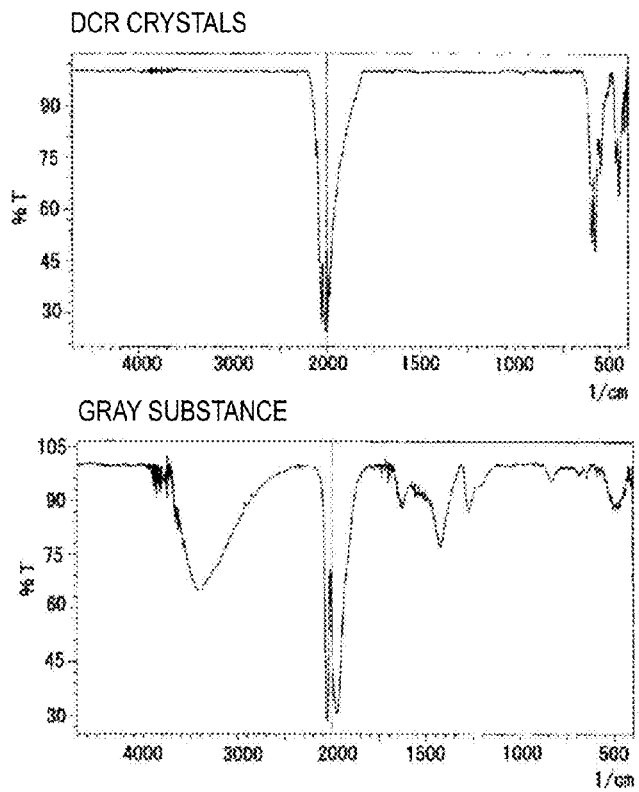
FIG. 3 shows IR results of DCR and by-products in the embodiment.
Figure 4:
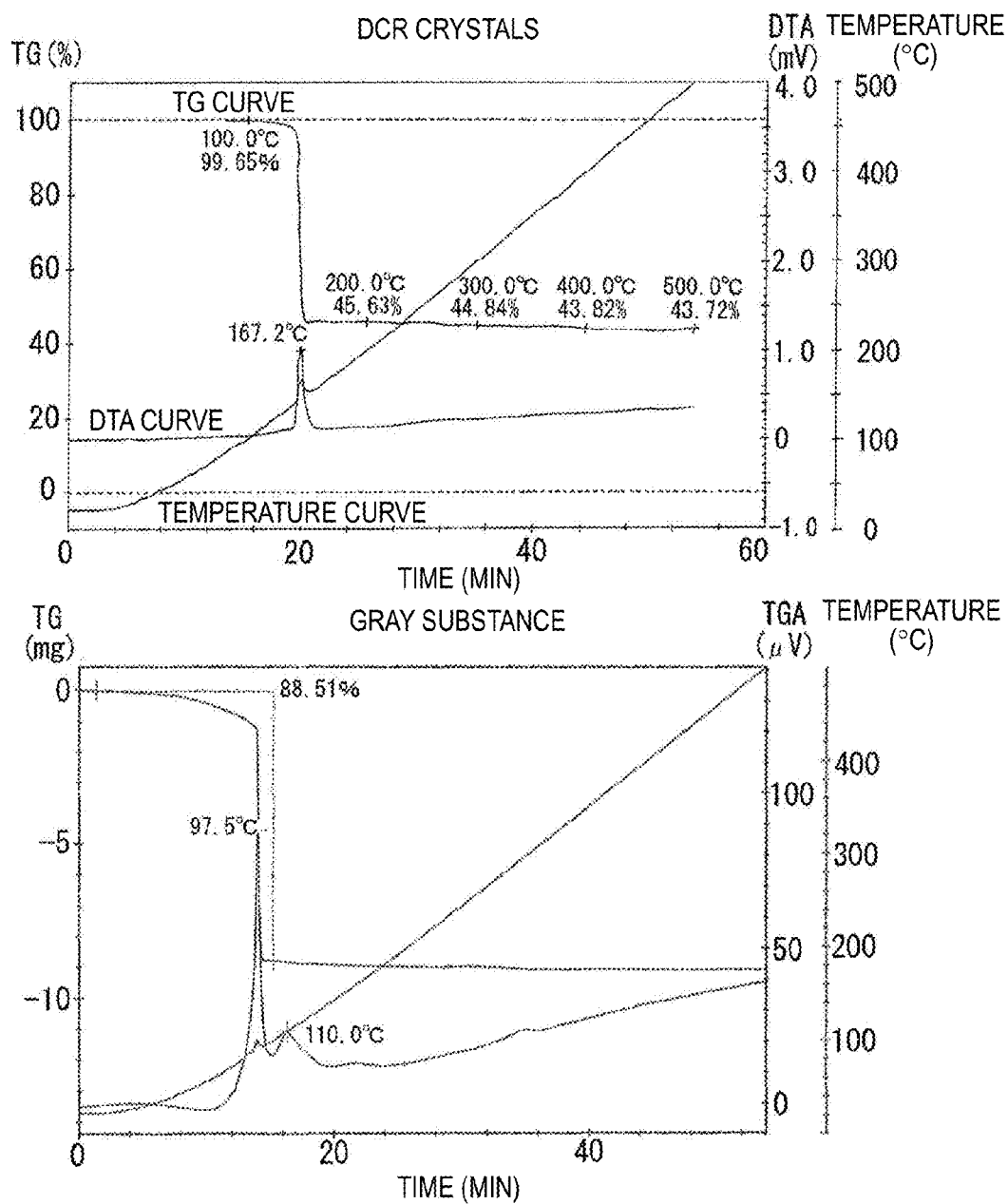
FIG. 4 shows TG-DTA results of DCR and by-products in the presence of Air in the embodiment.
Figure 5:
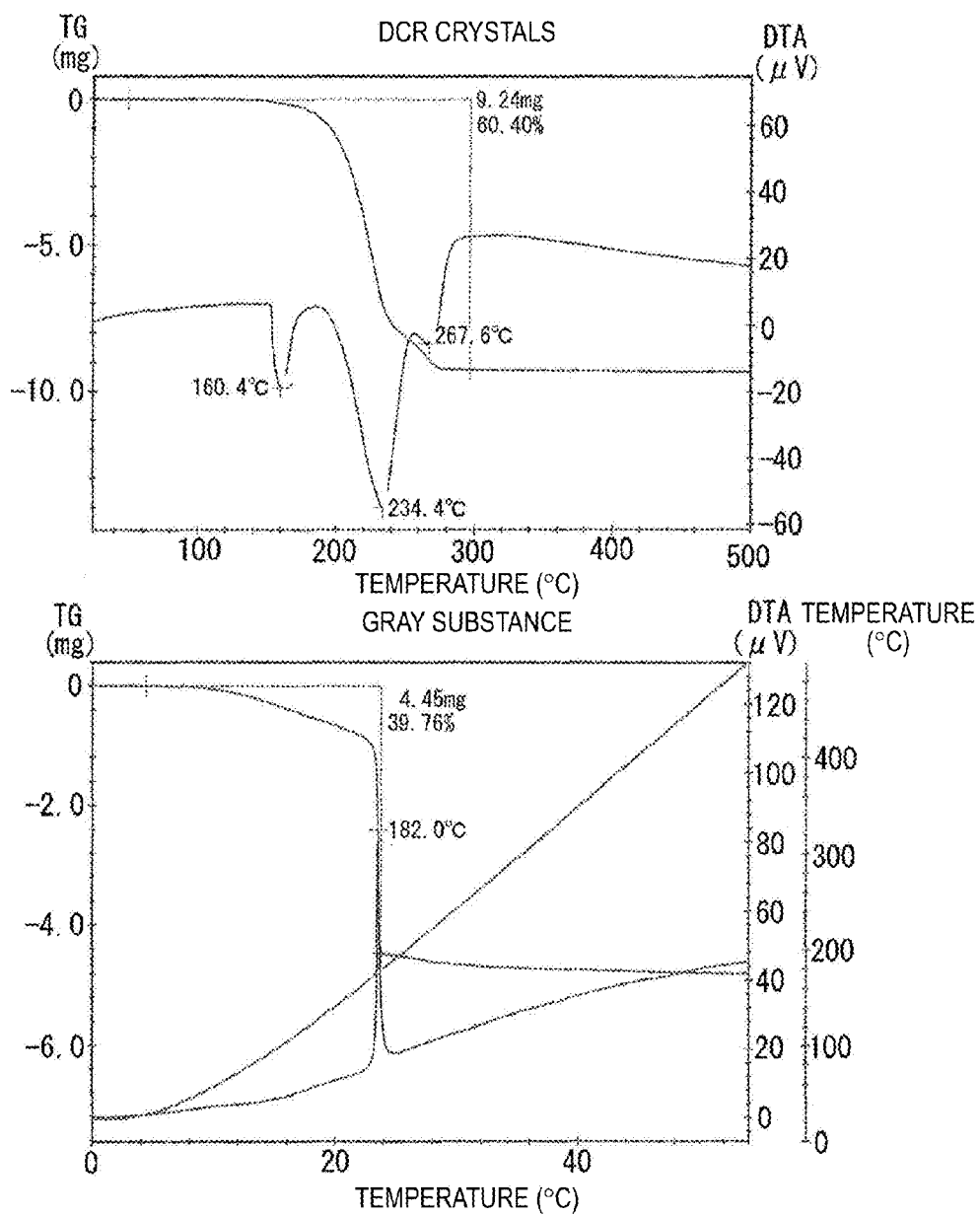
FIG. 5 shows TG-DTA results of DCR and by-products in an $N_2$ atmosphere in the embodiment.

16 g of the same DCR crystals as in the above Example were used. Without performing the nitrogen gas replacement of the distillation, dissolution, and crystallization tanks and the pressure reduction in the drying furnace, and without limiting the oxygen concentration, DCR was purified by a sublimation method and a recrystallization method. The amount of ethyl acetate used was 0.8 L. Other recrystallization conditions were the same as those in the Example. In the obtained DCR, a gray substance was present in orange crystals (DCR). This substance (gray substance) was collected. As a result, in 14.5 g of the obtained DCR crystals, the amount of gray substance contained was 0.2 g. The DCR crystals and gray substance were subjected to elemental analysis (CHN), IR analysis, and TG-DTA analysis to compare the characteristics. The TG-DTA analysis was performed under the following two kinds of measurement conditions: in the presence of Air (FIG. 4) and in an $N_2$ atmosphere (FIG. 5). The results are each shown in Table 3 and FIGS. 3 to 5.

TABLE 3

| | Results of elemental analysis % | | |
|---|---|---|---|
| | H | C | N |
| DCR crystals | 0 | 22.44 | 0 |
| Gray substance | 1.61 | 13.61 | 0 |

From the results of elemental analysis shown in the above table, it turned out that the gray substance was different from the DCR crystals in the proportions of constituent elements, and that in particular, hydrogen H, which is originally not contained in DCR, was present. Additionally, in the results of IR analysis shown in FIG. 3, the detection peak of the gray substance was obviously different from that of the DCR crystals. Additionally, in the results of TG-DTA measurement shown in FIGS. 4 and 5, the DCR crystals and the gray substance showed different detection peaks both in the presence of Air (FIG. 4) and in an $N_2$ atmosphere (FIG. 5).

From the above results, in Comparative Example 1 that did not control the oxygen concentration in the solvent or the atmosphere, a gray substance was contained in the DCR crystals after recrystallization. This gray substance showed characteristics obviously different from those of DCR in the proportions of elements, infrared absorption, and heat decomposability. In contrast, in the Example in which the dissolved oxygen concentration in the solvent was made 0.2 mg/L or less, and the oxygen concentration in the atmosphere was made 0.1 vol % or less, DCR crystals containing no gray substance were obtained.

Comparative Example 2

DCR was recrystallized by use of a mixed gas of 1% oxygen and 99% nitrogen in place of nitrogen gas (99.99% nitrogen) in the Example. In this comparative example, the inside of the equipment was not previously gas-purged, and ethyl acetate was placed in the equipment. Subsequently, the above gas was introduced into the dissolution tank (S) and crystallization tank (P) shown in FIG. 2 at 2 L/min to perform recrystallization. Other conditions were the same as in the method of the Example, and precipitated DCR crystals were collected by filtration.

The resulting DCR crystals were orange crystals as in the Example. However, as a result of checking the filter paper after filtration, a trace amount of black residue was present on the surface. Such a residue was not present at all in the Example. This showed that when a mixed gas containing 1% oxygen gas was used, a substance different from DCR crystals was formed.

Figure 6:
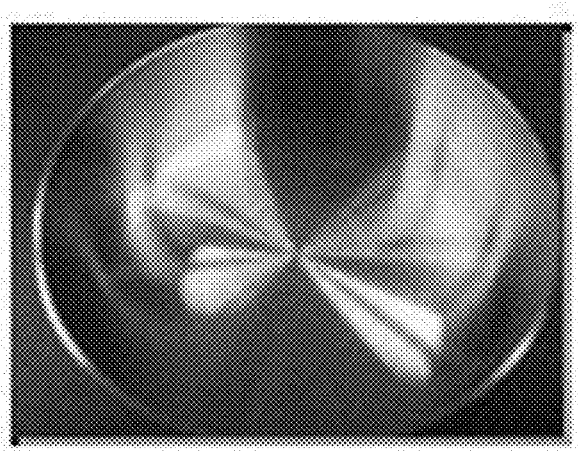
FIG. 6 is a photograph observing the inside of a reaction vessel after sublimation in the presence of 1% oxygen in the embodiment.
Figure 6:
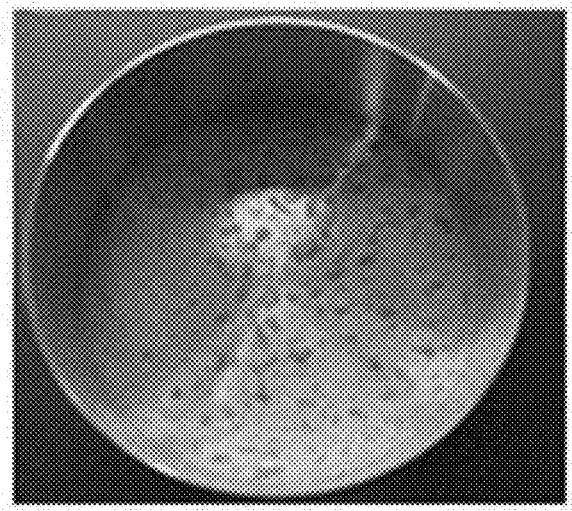

Next, as an additional experiment for checking the presence of substances other than DCR formed when a mixed gas containing 1% oxygen (99% nitrogen) was used, a sublimation test using the above oxygen-containing gas was performed. With use of the same mixed gas as in the above recrystallization test, the sublimation test was performed under the following conditions: temperature: 110° C., pressure: 0.2 torr, carrier gas (carbon monoxide, flow rate: 50 sccm), sublimation time: 24 hours, sample amount: 5 g. For comparison, the same sublimation test was also performed for the case of using nitrogen gas (99.99% nitrogen) as the purge gas. FIG. 6 shows a photograph observing the inside of the reaction vessel after the sublimation test.

From FIG. 6, it is considered that when nitrogen gas (99.99% nitrogen) was used, nothing remained in the reaction vessel after sublimation, indicating that DCR had been entirely sublimated. In contrast, when a mixed gas containing 1% oxygen (99% nitrogen) was used, a slight amount of residue was present in the reaction vessel. From above, it was confirmed that purification in the presence of 1% oxygen presence results in the formation of products other than DCR.

INDUSTRIAL APPLICABILITY

The present invention allows, in a method for purifying DCR using a recrystallization method, a trace amount of impurities in DCR to be reduced, while suppressing the formation of by-products. Additionally, the purification method of the present invention is also applicable to the recycling of used DCR recovered after chemical vapor deposition.

REFERENCE SIGNS LIST

D: Distillation tank
S: Dissolution tank
P: Crystallization tank
20: Valve
30: Filtration means

The invention claimed is:

1. A method for purifying dodecacarbonyl triruthenium (DCR), for purifying, by a recrystallization method, an organic ruthenium compound including DCR represented by a following formula as a raw material for chemical vapor deposition:

[Chemical Formula 1]

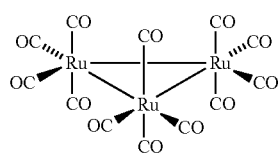

the method comprises a recrystallization step of purifying DCR by a recrystallization method,
the recrystallization step includes a dissolution stage of dissolving DCR in a solvent, a precipitation stage of precipitating DCR from the solvent, and a recovery stage of recovering the precipitated DCR, wherein
at least the dissolution stage is performed with a dissolved oxygen concentration in the solvent being 0.2 mg/L or less.

2. The method for purifying DCR according to claim 1, wherein at least the dissolution stage is performed in an atmosphere having an oxygen concentration of 0.1 vol % or less.

3. The method for purifying DCR according to claim 1, wherein the recrystallization step further includes a drying stage of drying the recovered DCR, and the drying stage is performed at a reduced pressure of 500 Pa or less.

4. The method for purifying DCR according to claim 1, wherein, in the dissolution stage, DCR is dissolved in at least one solvent selected from acetone, dichloromethane, DMF, ethyl acetate, chloroform, toluene, acetonitrile, and THF.

5. The method for purifying DCR according to claim 1, further comprising a stage of filtering the solvent with dissolved DCR after the dissolution stage and before the precipitation stage.

6. The method for purifying DCR according to claim 1, wherein the dissolution stage is performed at 55 to 130° C.

7. The method for purifying DCR according to claim 3, wherein the drying stage is performed at 0 to 40° C.

8. The method for purifying DCR according to claim 1, wherein the recrystallization step is performed after a sublimation step of purifying DCR by a sublimation method.

9. The method for purifying DCR according to claim 2, wherein the recrystallization step further includes a drying stage of drying the recovered DCR, and the drying stage is performed at a reduced pressure of 500 Pa or less.

10. The method for purifying DCR according to claim 2, wherein, in the dissolution stage, DCR is dissolved in at least one solvent selected from acetone, dichloromethane, DMF, ethyl acetate, chloroform, toluene, acetonitrile, and THF.

11. The method for purifying DCR according to claim 3, wherein, in the dissolution stage, DCR is dissolved in at least one solvent selected from acetone, dichloromethane, DMF, ethyl acetate, chloroform, toluene, acetonitrile, and THF.

12. The method for purifying DCR according to claim 2, further comprising a stage of filtering the solvent with dissolved DCR after the dissolution stage and before the precipitation stage.

13. The method for purifying DCR according to claim 3, further comprising a stage of filtering the solvent with dissolved DCR after the dissolution stage and before the precipitation stage.

14. The method for purifying DCR according to claim 4, further comprising a stage of filtering the solvent with dissolved DCR after the dissolution stage and before the precipitation stage.

15. The method for purifying DCR according to claim 2, wherein the dissolution stage is performed at 55 to 130° C.

16. The method for purifying DCR according to claim 3, wherein the dissolution stage is performed at 55 to 130° C.

17. The method for purifying DCR according to claim 4, wherein the dissolution stage is performed at 55 to 130° C.

18. The method for purifying DCR according to claim 5, wherein the dissolution stage is performed at 55 to 130° C.

19. The method for purifying DCR according to claim 4, wherein the drying stage is performed at 0 to 40° C.

20. The method for purifying DCR according to claim 2, wherein the recrystallization step is performed after a sublimation step of purifying DCR by a sublimation method.

* * * * *